(12) United States Patent
Nilsson et al.

(10) Patent No.: US 10,839,240 B2
(45) Date of Patent: Nov. 17, 2020

(54) METHOD OF ENROLLING A FINGERPRINT

(71) Applicant: FINGERPRINT CARDS AB, Gothenburg (SE)

(72) Inventors: René Nilsson, Eslöv (SE); Derek Hagen, Ytterby (SE)

(73) Assignee: FINGERPRINT CARDS AB, Gothenburg (SE)

( * ) Notice: Subject to any disclaimer, the term of this patent is extended or adjusted under 35 U.S.C. 154(b) by 0 days.

(21) Appl. No.: 16/622,690

(22) PCT Filed: Jun. 20, 2018

(86) PCT No.: PCT/SE2018/050662
§ 371 (c)(1),
(2) Date: Dec. 13, 2019

(87) PCT Pub. No.: WO2018/236280
PCT Pub. Date: Dec. 27, 2018

(65) Prior Publication Data
US 2020/0117931 A1    Apr. 16, 2020

(30) Foreign Application Priority Data

Jun. 22, 2017 (SE) ....................... 1750809

(51) Int. Cl.
*G06K 9/00* (2006.01)
(52) U.S. Cl.
CPC ..... *G06K 9/00926* (2013.01); *G06K 9/00013* (2013.01); *G06K 9/00087* (2013.01)
(58) Field of Classification Search
CPC ........... G06K 9/0006; G06K 9/00107; G06K 9/00926; G06K 9/00012; G06K 9/00013; G06K 9/00087; G06K 9/0004; A61B 5/1172; A61B 5/117; G06F 21/32
See application file for complete search history.

(56) References Cited

U.S. PATENT DOCUMENTS

| | | |
|---|---|---|
| 2003/0025897 A1 | 2/2003 | Iwai |
| 2006/0110015 A1 | 5/2006 | Rowe |
| 2006/0115128 A1 | 6/2006 | Mainguet |
| 2008/0037001 A1* | 2/2008 | Yokoyama ......... G06K 9/00912 356/51 |
| 2009/0166411 A1 | 7/2009 | Kramer et al. |
| 2010/0315337 A1 | 12/2010 | Ferren et al. |
| 2016/0148036 A1 | 5/2016 | Kim et al. |
| 2017/0270342 A1* | 9/2017 | He .................... G06F 21/32 |

FOREIGN PATENT DOCUMENTS

EP    2393040 B1    4/2013

OTHER PUBLICATIONS

PCT International Search Report and Written Opinion dated Aug. 1, 2018 for International Application No. PCT/SE2018/050662, 10 pages.

* cited by examiner

*Primary Examiner* — Koosha Sharifi-Tafreshi
(74) *Attorney, Agent, or Firm* — RMCK Law Group, PLC

(57) ABSTRACT

The present invention relates to a method of enrolling a fingerprint of a user's finger, by means of a fingerprint detection arrangement. In particular, the fingerprint detection arrangement comprises a fingerprint sensor and an optical sensor comprising a light emitting source and a light receiving device.

16 Claims, 6 Drawing Sheets

METHOD OF ENROLLING A FINGERPRINT

CROSS-REFERENCE TO RELATED APPLICATIONS

This application is a 371 U.S. National Stage of International Application No. PCT/SE2018/050662, filed Jun. 20, 2018, which claims priority to Swedish Patent Application No. 1750809-4, filed Jun. 22, 2017. The disclosures of each of the above applications are incorporated herein by reference in their entirety.

FIELD OF THE INVENTION

The present invention relates to a method of enrolling a fingerprint of a user's finger. More particularly, the present invention relates to method of enrolling a fingerprint of a user's finger using a fingerprint sensor as well as an optical sensor. The invention also relates to a method for authenticating a user of an electronic device.

TECHNICAL BACKGROUND

Various types of biometric systems are used more and more in order to provide an increased security for accessing an electronic device and at the same time keep the user convenience at an acceptable level. In particular fingerprint sensors have been successfully integrated in such devices, for example, thanks to their small form factor, high performance and user acceptance.

In a fingerprint sensor, a captured image is compared to one or more stored fingerprint templates in order to verify the identity of the user. In order to avoid performing matching on an image which is of low quality, where it is likely that no successful matching can be performed, a quality metric is assigned to the captured image before matching to determine if the specific image should proceed to the matching step.

However, a problem that might occur is that a so-called spoof fingerprint is used for trying to gain access to the electronic device. Thus, there is a continuous demand to prevent unauthorized users from gaining access to the electronic device via the fingerprint sensor.

SUMMARY OF THE INVENTION

In view of the above-mentioned desired properties and other drawbacks, it is an object of the present invention to provide an improved method of enrolling a fingerprint of a user's finger.

According to a first aspect, there is provided a method of enrolling a fingerprint of a user's finger, by means of a fingerprint detection arrangement comprising a fingerprint sensor and an optical sensor comprising a light emitting source and a light receiving device, the method comprising the steps of capturing, by the fingerprint sensor, a first enrollment image of a fingerprint of a user's finger placed on the fingerprint sensor at a first position thereon; emitting light, by the light emitting source of the optical sensor, towards the user's finger; receiving, by the light receiving device, at least a portion of the light emitted by the light emitting source when the finger is placed at the first position on the fingerprint sensor; determining a first light response profile based on the light received by the light receiving device; and forming a fingerprint template comprising a fingerprint representation based on the first enrollment image and the first light response profile when the finger is placed at the first position.

The wording "a first enrollment image" should in the following be understood to include an image extracted from the fingerprint of the user's finger when the finger is placed at the first position on the fingerprint sensor. Hence, the first enrollment image corresponds to information extracted from the fingerprint image when the finger is placed at the single first position on the fingerprint sensor.

Moreover, the light emitting source should be understood to mean a device which is able to emit light towards the user's finger. Such light emitting source may also be referred to as an emitter, or light emitter. The light emitting source may preferably be a light emitting device (LED). Other alternative light emitting sources are of course conceivable. The light receiving device should thus be understood to mean a device which is able to receive the light emitted from the light emitting source. The light receiving device should receive the light emitted by the light emitting source after the light has interacted with the finger. The light receiving device may also be referred to as a detector, or a light detector. The light emitting source and the light receiving device may be positioned spaced apart from each other in the fingerprint detection arrangement. The light emitting source and the light receiving device may also be positioned in the vicinity of each other, such as side by side to each other. In the latter case, the light receiving device receives light reflected from the fingerprint of the user's finger. As will also be described further below, the fingerprint detection arrangement may comprise a plurality of light emitting sources and a plurality of light receiving devices. The plurality of light emitting sources and the plurality of light receiving devices may be controllable to be selectively actuated. Hence, one of the plurality of light emitting sources may be arranged to emit light when the finger is placed at a certain position on the fingerprint sensor, while another one of the plurality of light emitting sources may be arranged to emit light when the finger is placed at another position on the fingerprint sensor. The same applies for the plurality of light receiving devices.

Furthermore, the fingerprint detection arrangement may comprise a light guiding structure through which the light emitted from the light emitting source is propagating before being received by the light receiving device. Hereby, light is emitted from the light emitting source through the light guiding structure towards the user's finger, which finger is placed at an upper surface of the light guiding structure. At least a portion of the emitted light is thereafter interacting with the user's finger where after light is received by the light receiving device. The light guiding structure may also be referred to as a light guiding element or light guiding layer, etc.

Still further, the wording "light response profile" relates to the characteristics of at least the light received by the light receiving device. Preferably, the characteristic of the light received by the light receiving device is compared to the characteristic of the light emitted from the light emitting source. Hereby, a light response profile can be determined. Examples of the light response profile will be given below.

Moreover, the step of forming the fingerprint template thus comprises a combination of the enrollment image from the fingerprint sensor and the light response profile. Hence, for each position of the finger on the fingerprint sensor, an enrollment image and a light response profile is formed. In further detail, when positioning the finger at the first position, a first enrollment image is captured and a first light response profile is determined. The fingerprint template thus comprises data for these two variables for each position of the finger thereof. The fingerprint template formed may thus be referred to as a first fingerprint sub template, where each sub template comprises an enrollment image and a corresponding light response profile.

The present invention is based on the insight that the light response profile will be different in dependence of the position of the finger on the fingerprint sensor. Thus, the profile, or characteristics, of the light received by the light receiving device will depend on the specific position of the finger on the fingerprint sensor. This is due to the fact the characteristic of the light, after the light has interacted with the finger will be different depending on the specific position of the finger as light will reflect from, or transmit through, the finger differently for different positions of the finger. The characteristics of the light will also be dependent on the pressure the finger exposes to the fingerprint sensor. An advantage is thus that a combination of enrollment image and metadata in the form of a light response profile is provided for each position of the finger in the fingerprint template. Hereby, further security of unauthorized users trying to gain access to e.g. an electronic device via the fingerprint detection arrangement is provided, since improved accuracy of measurement is provided using two different sensors. Also, the evaluation of the light response profile may reduce the risk of a spoof fingerprint gaining access via the fingerprint detection arrangement. Hence, an improved performance by the optical sensor is achieved.

According to an example embodiment, the step of forming the fingerprint template may further comprise the step of combining the first enrollment image and the first light response profile when the finger is placed at the first position of the fingerprint sensor.

According to an example embodiment, the step of determining the first light response profile may be further based on the light emitted by the light emitting source. As briefly described above, the characteristic of the light received by the light receiving device may be compared to the characteristic of the light emitted by the light emitting source. Hereby, a light response profile may be formed based on the difference in characteristic between the light received by the light receiving device and the characteristic of the light emitted by the light emitting source, wherein the light response profile is different depending on the specific position of the finger on the fingerprint sensor.

According to an example embodiment, the step of determining the first light response profile may comprise the steps of determining an emitted light intensity of the light emitted by the light emitting source; determining a received light intensity of the light received by the light receiving device; comparing the received light intensity with the emitted light intensity; and determining the first light response profile based on a difference in light intensity between the received light intensity and the emitted light intensity.

The wording "light intensity" may be understood as the energy of the light emitted from the light emitting source. Such energy may be referred as radiant energy.

The emitted light will, when interacting with the finger, change its intensity. Hereby, a comparison of the intensity of the received light and the intensity of the emitted light can be made to determine the light response profile.

According to an example embodiment, the light emitting device may be arranged to emit light of at least two distinct wavelengths, and the light receiving device is arranged to receive at least a portion of the light of the at least two distinct wavelengths.

Hereby, the difference in light intensity for the light of each of the at least two different distinct wavelengths may be used for determining the light response profile. Hence, the received light from a first wavelength is compared to the emitted light of the same first wavelength, and received light from a second wavelength is compared to the emitted light of the same second wavelength.

According to an example embodiment, the method may further comprise the step of determining the first position on the fingerprint sensor based on the enrollment image captured by the fingerprint sensor. Thus, the fingerprint sensor determines the position of the finger positioned thereon. A control unit or the like may thus receive the image from the fingerprint sensor and set the image as the image for the first position. The control unit also receives a light response profile which is set as a light response profile for the first position. Hereby, and as described above, the first position of the finger on the fingerprint sensor comprises an enrollment image as well as metadata in the form of a light response profile.

According to an example embodiment, the optical sensor may be a first optical sensor comprising a first light emitting source and a first light receiving device, wherein the fingerprint detection arrangement further comprises a second optical sensor comprising a second light emitting source and a second light receiving device, wherein the method further comprises the steps of comparing the determined first position on the fingerprint sensor with at least a first and a second pre-set finger position on the fingerprint sensor; controlling the first optical sensor to emit light by the first light emitting source and to receive at least a portion of the emitted light by the first light receiving device if the first position substantially corresponds to the first pre-set finger position.

Hereby, either the first or the second optical sensor may be used for determining the light response profile based on the position of the finger on the fingerprint sensor. An advantage is that a more distinct optical response signal may be received by the first optical sensors when the position of the finger corresponds to the first pre-set finger position in comparison to the response signal received by the second optical sensor for such position of the finger.

According to an example embodiment, the method may further comprise the step of inhibiting the second optical sensor from emitting light if the first position substantially corresponds to the first pre-set finger position.

According to an example embodiment, the method may further comprise the steps of capturing, by the fingerprint sensor, a second enrollment image of the fingerprint of the user's finger placed on the fingerprint sensor at a second position thereon, said second position being different in comparison to the first position; emitting light, by the light emitting source of the optical sensor, towards the user's finger; receiving, by the light receiving device, at least a portion of the light emitted by the light emitting source when the finger is placed at the second position on the fingerprint sensor; and determining a second light response profile based on the light received by the light receiving device when the finger is placed at the second position on the fingerprint sensor; wherein the step of forming the fingerprint template further comprising a fingerprint representation based on the second enrollment image and the second light response profile when the finger is placed at the second position.

Hereby, a second, different fingerprint representation will be provided to the fingerprint template. The second fingerprint representation thus comprises an enrollment image from the fingerprint sensor for the second position of the finger, as well as a corresponding second light response profile.

According to an example embodiment, the second position of the user's finger may correspond to a position being rotated on a surface of the fingerprint sensor relative to the first position. According to an example embodiment, the second position of the user's finger may correspond to a position being moved along a surface of the fingerprint sensor relative to the first position. Hereby, the fingerprint sensor detects the different positions of the finger.

According to an example embodiment, the fingerprint sensor may be one of a capacitive fingerprint sensor and an ultrasound fingerprint sensor.

According to a second aspect, there is provided a method for authenticating a user of an electronic device comprising a fingerprint detection arrangement, the fingerprint detection arrangement comprising a fingerprint sensor and an optical sensor comprising a light emitting source and a light receiving device, the method comprising the steps of receiving, by the fingerprint sensor, a first authentication image of a fingerprint of a user's finger placed on the fingerprint sensor; emitting light, by the light emitting source of the optical sensor, towards the user's finger; receiving, by the light receiving device, at least a portion of the light emitted by the light emitting source when the finger is placed on the fingerprint sensor; determining a first light authentication response profile based on the light received by the light receiving device; and matching the first authentication image and the first light authentication response profile against a fingerprint template for authenticating the user, wherein the fingerprint template comprises a fingerprint representation for a finger of the user for at least one previously enrolled position of the finger at the fingerprint sensor and an associated light response profile.

Effects and features of the second aspect are largely analogous to those described above in relation to the first aspect. Hence, by matching the first authentication image and the first light authentication response profile against at least one previously enrolled position of the finger at the fingerprint sensor and an associated light response profile, the risk of a user having a spoof fingerprint for gaining access to the electronic device is reduced.

According to an example embodiment, the step of matching the first authentication image and the first light authentication response profile against the fingerprint template may further comprise the step of determining a position of the finger on the fingerprint sensor based on the first authentication image of the fingerprint. Hereby, when determining the position of the finger on the fingerprint sensor, a corresponding enrolled position of the fingerprint may be acquired for comparison.

According to an example embodiment, the step of matching the first authentication image and the first light authentication response profile against the fingerprint template may further comprise the step of determining a correspondence between the determined position of the finger on the fingerprint sensor and the fingerprint representation for the finger of the user for the at least one previously enrolled position.

Hereby, if the finger is placed at a position on the fingerprint sensor at which there are no enrollment image and optical response profile available, a best match with at least one enrolled position will be made. If the finger is placed at a position between two enrolled positions, an interpolation of the enrolled images and the optical response profiles for these two enrolled positions may be made for authenticating the user. The best match may be a predetermined threshold value for the fingerprint image and the optical response profile, respectively.

According to third aspect, there is provided a fingerprint detection arrangement comprising a fingerprint sensor and an optical sensor, said optical sensor comprising a light emitting source and a light receiving device, and a control unit connected to the fingerprint sensor and said optical sensor, wherein, when a user enrolls a fingerprint, the control unit is configured to control the fingerprint sensor to capture a first enrollment image of a fingerprint of a user's finger when the finger is placed on the fingerprint sensor at a first position thereon; control the light emitting source of the optical sensor to emit light towards the user's finger; control the light receiving device to receive at least a portion of the light emitted by the light emitting source when the finger is placed at said first position on the fingerprint sensor; determine a first light response profile based on the light received by the light receiving device; and form a fingerprint template comprising a fingerprint representation based on the first enrollment image and the first light response profile when the finger is placed at the first position.

Effects and features of the third aspect are largely analogous to those described above in relation to the first and second aspects.

According to a fourth aspect, there is provided a fingerprint detection arrangement of an electronic device, the fingerprint detection arrangement comprising a fingerprint sensor and an optical sensor, said optical sensor comprising a light emitting source and a light receiving device, and a control unit connected to the fingerprint sensor and said optical sensor, wherein, when authenticating a user of the electronic device, the control unit is configured to control the fingerprint sensor to receive a first authentication image of a fingerprint of a user's finger when the finger is placed on the fingerprint sensor; control the light emitting source of the optical sensor to emit light towards the user's finger; control the light receiving device to receive at least a portion of the light emitted by the light emitting source when the finger is placed at said first position on the fingerprint sensor; determine a first light authentication response profile based on the light received by the light receiving device; and match the first authentication image and the first light authentication response profile against a fingerprint template for authenticating the user, wherein the fingerprint template comprises a fingerprint representation for a finger of the user for at least one previously enrolled position of the finger at the fingerprint sensor and an associated light response profile.

Effects and features of the fourth aspect are largely analogous to those described above in relation to the first and second aspects.

In the context of the present application, the "enrollment image" and/or the "authentication image" of a fingerprint image may be any information extracted from the fingerprint image, which is useful for assessing the similarity between fingerprint images acquired at different times. For instance, the enrollment/authentication image of the fingerprint may comprise descriptions of fingerprint features (such as so-called minutiae) and information about the positional relationship between the fingerprint features. Alternatively, the representation of the fingerprint image may be the image itself, or a compressed version of the image. For example, the image may be binarized and/or skeletonized. Various ways of extracting such authentication image or enrollment image from a fingerprint image are well-known to a person of ordinary skill in the relevant art.

Further features of, and advantages with, the present invention will become apparent when studying the appended claims and the following description.

The skilled person realize that different features of the present invention may be combined to create embodiments other than those described in the following, without departing from the scope of the present invention.

BRIEF DESCRIPTION OF THE DRAWINGS

These and other aspects of the present invention will now be described in more detail with reference to the appended drawings showing example embodiments of the invention, wherein.

DETAILED DESCRIPTION OF PREFERRED EMBODIMENTS OF THE INVENTION

Figure 1:
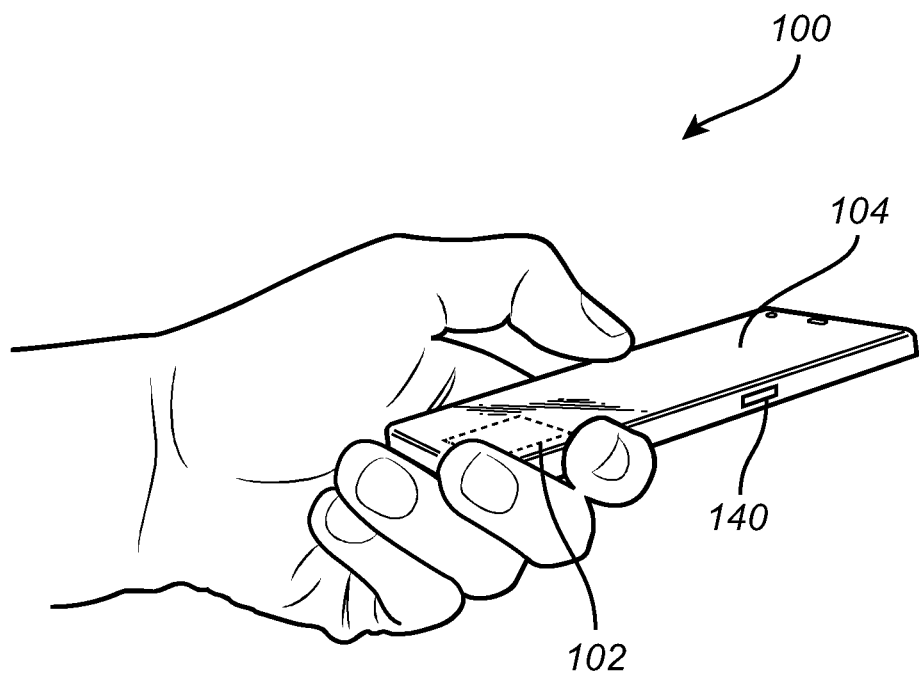
FIG. 1 schematically exemplifies an electronic device according to the present invention, in the form of a mobile phone comprising an integrated fingerprint detection arrangement.

The present invention will now be described more fully hereinafter with reference to the accompanying drawings, in which exemplary embodiments of the invention are shown. The invention may, however, be embodied in many different forms and should not be construed as limited to the embodiments set forth herein; rather, these embodiments are provided for thoroughness and completeness. Like reference character refer to like elements throughout the description.

FIG. 1 is a perspective view of a schematic illustration of an electronic device 100 comprising a fingerprint detection arrangement 102 and a touch sensor 104. The electronic device 100 is in FIG. 1 depicted as a handheld electronic device in the form of a mobile phone. However, it should be readily understood that the invention is equally applicable for other types of electronic devices such as e.g. a wearable device, a tablet, etc. Thus, the fingerprint detection arrangement 102 can be used for such electronic devices requiring a way to identify and/or authenticate a user. The electronic device 100 further comprises a control unit 140 connected to below described fingerprint sensor 101 and optical sensor 130. The control unit 140 is merely schematically illustrated for simplicity of understanding.

Figure 2:
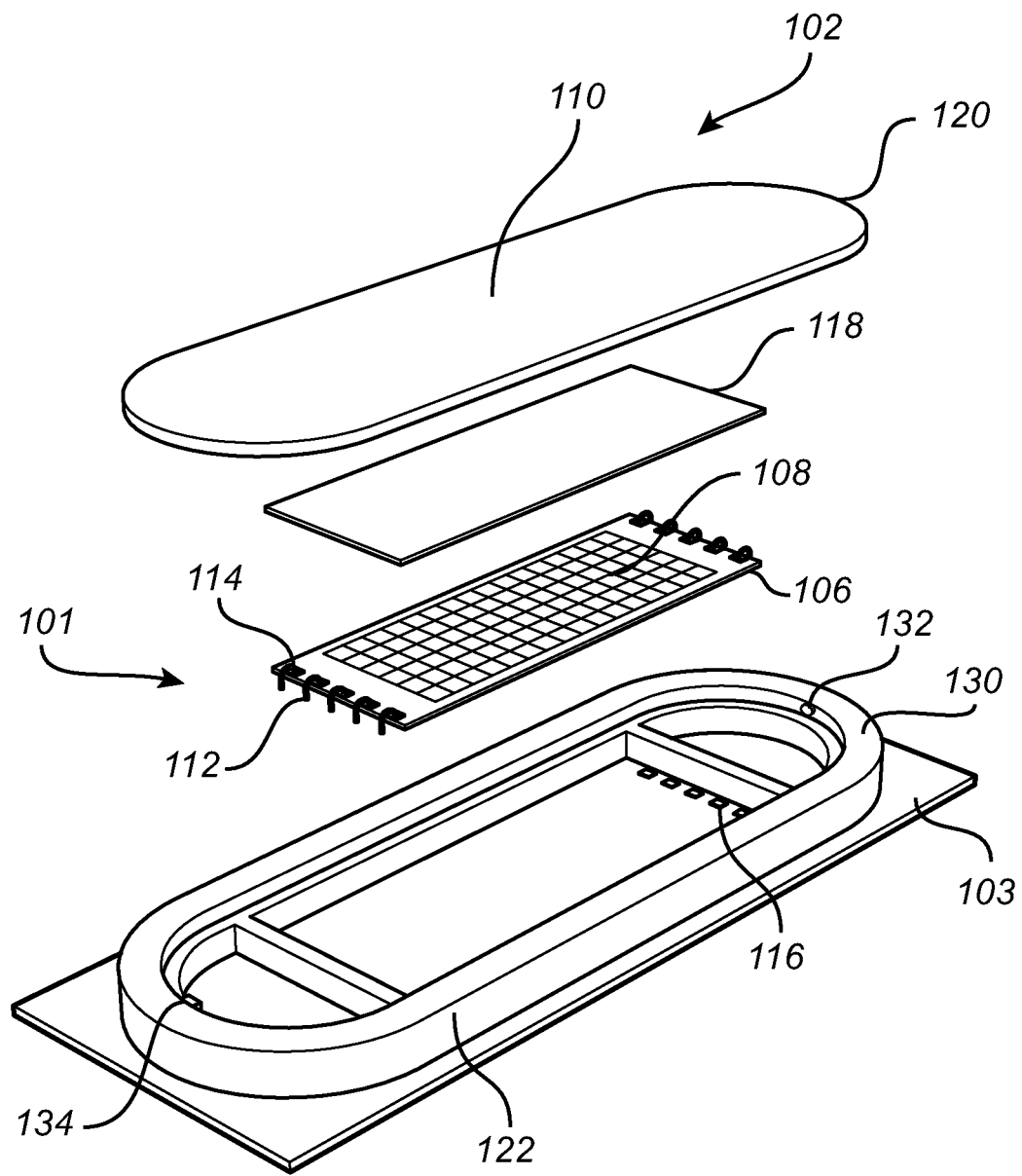
FIG. 2 is an exploded view of a fingerprint detection arrangement according to an example embodiment.

With reference to FIG. 2, a schematic illustration of an exploded view of an example embodiment of the fingerprint detection arrangement 102 is depicted. The fingerprint detection arrangement 102 in FIG. 2 comprises a fingerprint sensor 101 for capturing an image of a user's finger. The fingerprint sensor comprises a substrate 103 comprising readout circuitry (also referred to as a control unit, not shown) for reading information provided by a fingerprint sensing chip 106 which is arranged on the substrate 103. The substrate 103 may be a conventional printed circuit board (PCB), a flexible substrate, or any other type of substrate or carrier suitable for use in the application at hand.

Moreover, the sensing chip 106 further comprises a plurality of sensing elements 108 having a surface defining a sensing plane. Each sensing element 108 is configured to provide a signal indicative of an electromagnetic coupling between the sensing element and a finger placed on the exterior surface 110 of the fingerprint sensing device 102. The signal from each of the sensing elements 108 is provided to the readout circuitry of the substrate by means of a plurality of bond wires 112 arranged between a set of respective first bond pads 114 located on the sensing chip 106 and a set of respective second bond pads 116 located on the substrate 103, thereby electrically connecting the sensing chip 106 to the readout circuitry of the substrate 103. The signal from the sensing elements 108 may, instead of the bond wires 112, be connected to the readout circuit of the substrate 103 by means of vertical interconnection access (VIA) through the sensing chip 106, etc.

As is further depicted in FIG. 2, the fingerprint sensor 101 comprises an adhesive 118 for mechanically attaching a light guiding structure 120 in the form of a protective plate to the sensing chip 106. The adhesive is schematically illustrated as having the same size and shape as the sensing chip 106. The light guiding structure 120 may constitute any type of insulating transparent or semi-transparent material such as e.g. glass material or a polymeric material, or equivalents thereof, which material is suitable for use as a top layer forming a surface in a fingerprint sensing device.

Still further, the exemplifying fingerprint detection arrangement 102 depicted in FIG. 2 comprises a surrounding frame 122 which is arranged to fully surround and encircle the sensing chip 106. Moreover, the fingerprint detection arrangement 102 comprises an optical sensor 130 connected on an interior surface of the surrounding frame 122. The optical sensor 130 comprises a light emitting source 132 and a light receiving device 134. Hereby, and as will be described in further detail below with reference to the description of FIGS. 3a and 3b, the light emitting source 132 is arranged to emit light through the light guiding structure 120 and the light receiving device 134 is arranged to receive the emitted light 132 after the light has interacted with the finger when the finger is placed on the exterior surface 110.

The fingerprint sensor 101 in FIG. 2 is preferably a capacitive fingerprint sensor, although it should be readily understood that other alternatives are conceivable, such as e.g. an ultrasonic fingerprint sensor, etc.

Figure 3A:
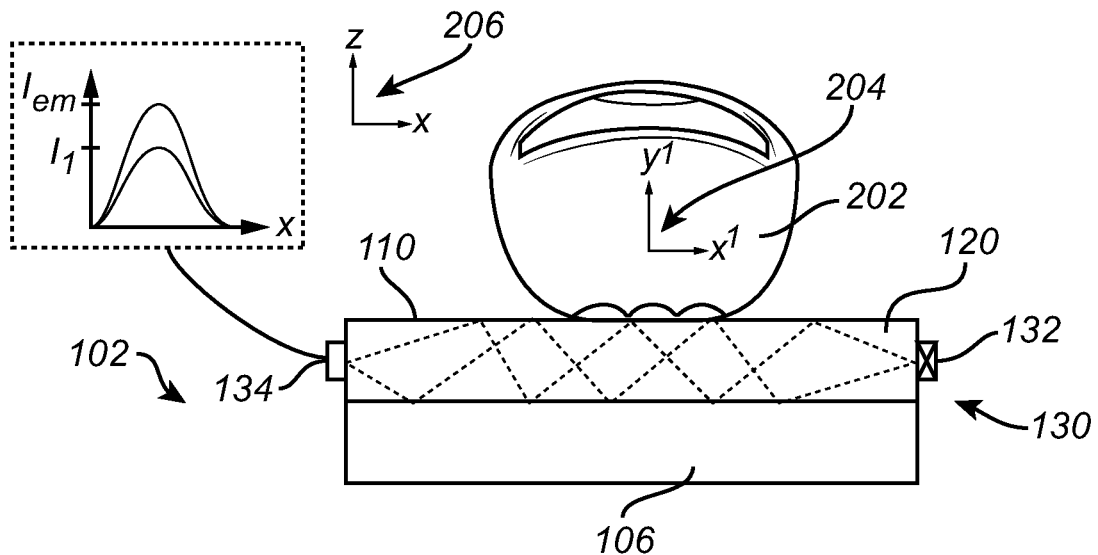
FIGS. 3a-3b schematically illustrate example embodiments of the fingerprint detection arrangement when the finger is placed on the fingerprint sensor at two different positions.
Figure 3B:
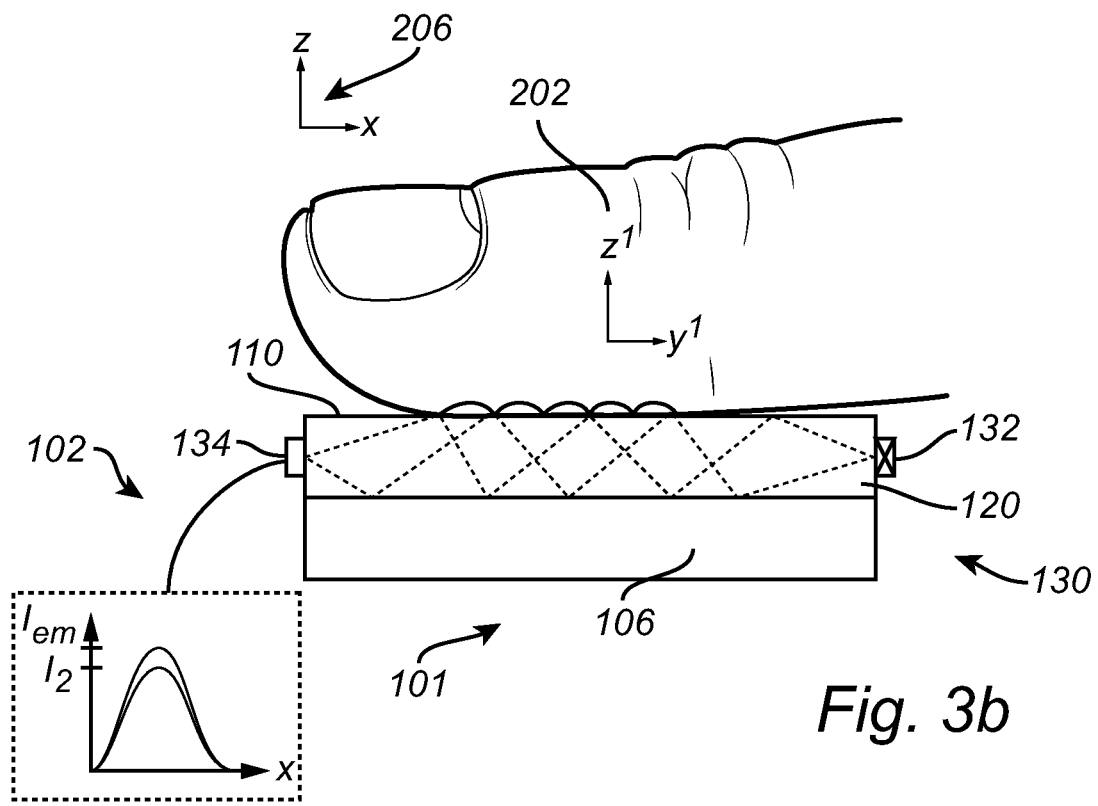

With reference to FIGS. 3a and 3b, further detailed description of the functionality of the optical sensor 130 in connection to the use of the fingerprint sensor 101 is provided. In FIGS. 3a and 3b, the substrate 103, sensing elements 108, the bond wires 112, the adhesive layer 118, as well as the surrounding frame 122 has been omitted for improving the illustration of the functionality of the fingerprint detection arrangement 102.

Reference is first made to FIG. 3a which schematically illustrates a finger 202 placed on the exterior surface 110 at a first position thereon. The first position of the finger 202 is here defined by means of a finger coordinate system 204 relative to a fingerprint detection arrangement coordinate system 206. In the example embodiment depicted in FIG. 3a, the finger 202 is positioned on the exterior surface 110 such that the $x^1$-axis of the finger 202 corresponds to the x-axis of the fingerprint detection arrangement, and the $z^1$-axis of the finger 202 corresponds to the z-axis of the fingerprint detection arrangement.

When the finger 202 is positioned at the first position on the exterior surface 110, the fingerprint sensor 101 captures an image of the fingerprint and at substantially the same time, the light emitting source 132 emits light through the light guiding structure 120 towards the user's finger 202. After the emitted light has interacted with the finger 202 it is received by the light receiving device 134. The intensity of the received light, in FIG. 3a denoted as $I_1$ is compared to the intensity of the emitted light, denoted as $I_{em}$, such that a first light response profile can be determined. According to the example depicted in FIG. 3a, the light intensity $I_1$ of the received light is lower in comparison to the light intensity $I_{em}$ of the emitted light, although the wavelength is kept the same.

Reference is now made to FIG. 3b, which schematically illustrates the finger 202 placed on the exterior surface 110 at a second position thereon. In the example embodiment depicted in FIG. 3b, the finger 202 is positioned on the exterior surface 110 such that the $y^1$-axis of the finger 202 corresponds to the x-axis of the fingerprint detection arrangement, and the $z^1$-axis of the finger 202 corresponds to the z-axis of the fingerprint detection arrangement 102. In a similar manner as described above in relation to the description of FIG. 3a, when the finger 202 is positioned at the second position on the exterior surface 110, the fingerprint sensor 101 captures an image of the fingerprint and at substantially the same time, the light emitting source 132 emits light through the light guiding structure 120 towards the user's finger 202. After the emitted light has interacted with the finger 202 it is received by the light receiving device 134. The intensity of the received light, in FIG. 3b denoted as $I_2$ is compared to the intensity of the emitted light, denoted as $I_{em}$, such that a second light response profile can be determined. According to the example depicted in FIG. 3b, the light intensity $I_2$ of the received light is lower in comparison to the light intensity $I_{em}$ of the emitted light, although the wavelength is kept the same.

When comparing the first and second light response profiles in FIGS. 3a-3b, i.e. the comparison between the light intensity $I_1$ of the received light for the first position and the light intensity $I_2$ of the received light for the second position, it can be seen that the light intensities differ in dependence of the position of the finger 202. In the examples depicted in FIGS. 3a and 3b, the light intensity is higher for the second position in comparison to the first position.

It should be readily understood that the $x^1$-axis and the $y^1$-axis of the finger coordinate system 204 may naturally also be positioned at any angle relative to the x-axis and y-axis of the fingerprint detection arrangement coordinate system 206.

Moreover, the light intensity of the light received by the light receiving device 134 may also be dependent on the pressure exposed by the finger on the exterior surface 110, as well as how large area of the finger being in contact with the exterior surface 110. The pressure can be determined by means of the fingerprint sensor. If the pressure is too high, the user may be requested to re-position the finger on the fingerprint sensor.

Figure 4:
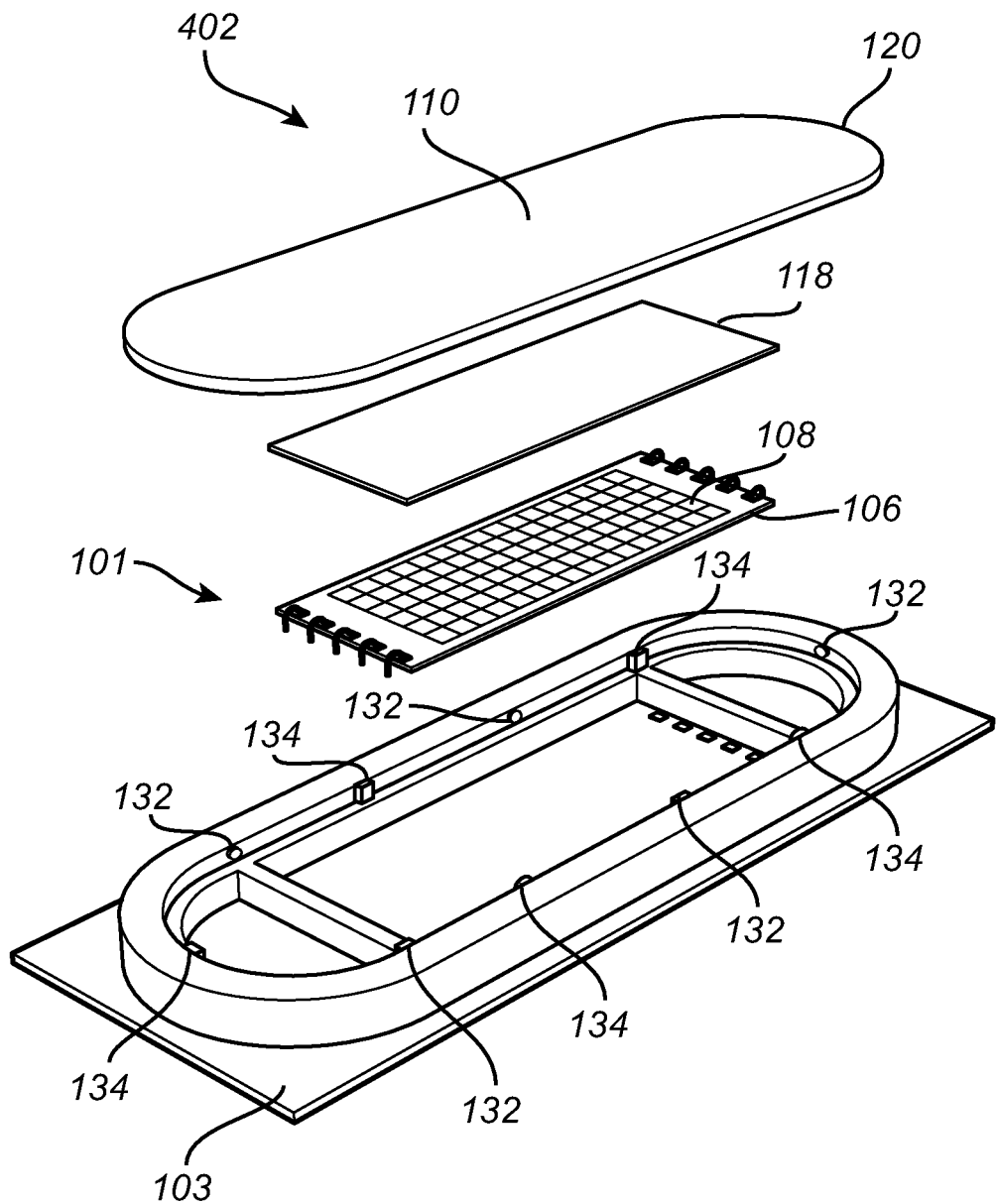
FIG. 4 is an exploded view of a fingerprint detection arrangement according to another example embodiment.

With reference to FIG. 4, a schematic illustration of an exploded view of another example embodiment of the fingerprint detection arrangement 402 is depicted. The difference between the embodiment depicted in FIG. 4 and the embodiment depicted in FIG. 2 is that the fingerprint detection arrangement 402 in FIG. 4 comprises a plurality of optical sensors, and hence a plurality of light emitting sources 132 and a plurality of light receiving devices 134. In the embodiment depicted in FIG. 4, the plurality of light emitting sources 132 and the plurality of light receiving devices 134 are alternatingly arranged around the surrounding frame 122.

By means of the embodiment depicted in FIG. 4, the plurality of light emitting sources 132 and the plurality of light receiving devices 134 can be selectively activated, preferably in dependence of the position of the finger on the fingerprint sensor 101. Hence, the specific position of the finger on the fingerprint sensor 101 can be determined by capturing an image of the fingerprint, where after it is determined which one, or which ones, of the plurality of light emitting sources 132 and the plurality of light receiving devices 134 to be operated when determining the light response profile.

Figure 5:
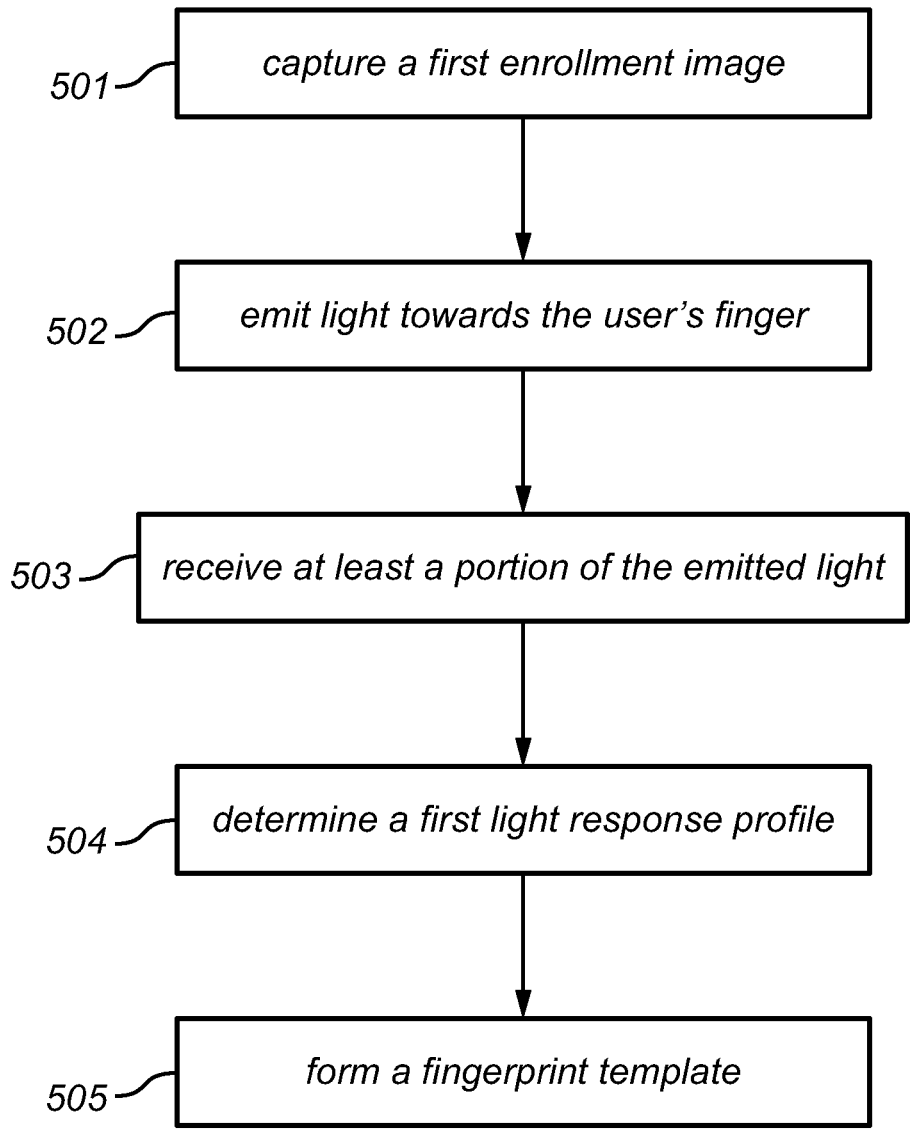
FIG. 5 is a flow chart of a method of enrolling a fingerprint of a user's finger according to an example embodiment.
Figure 6:
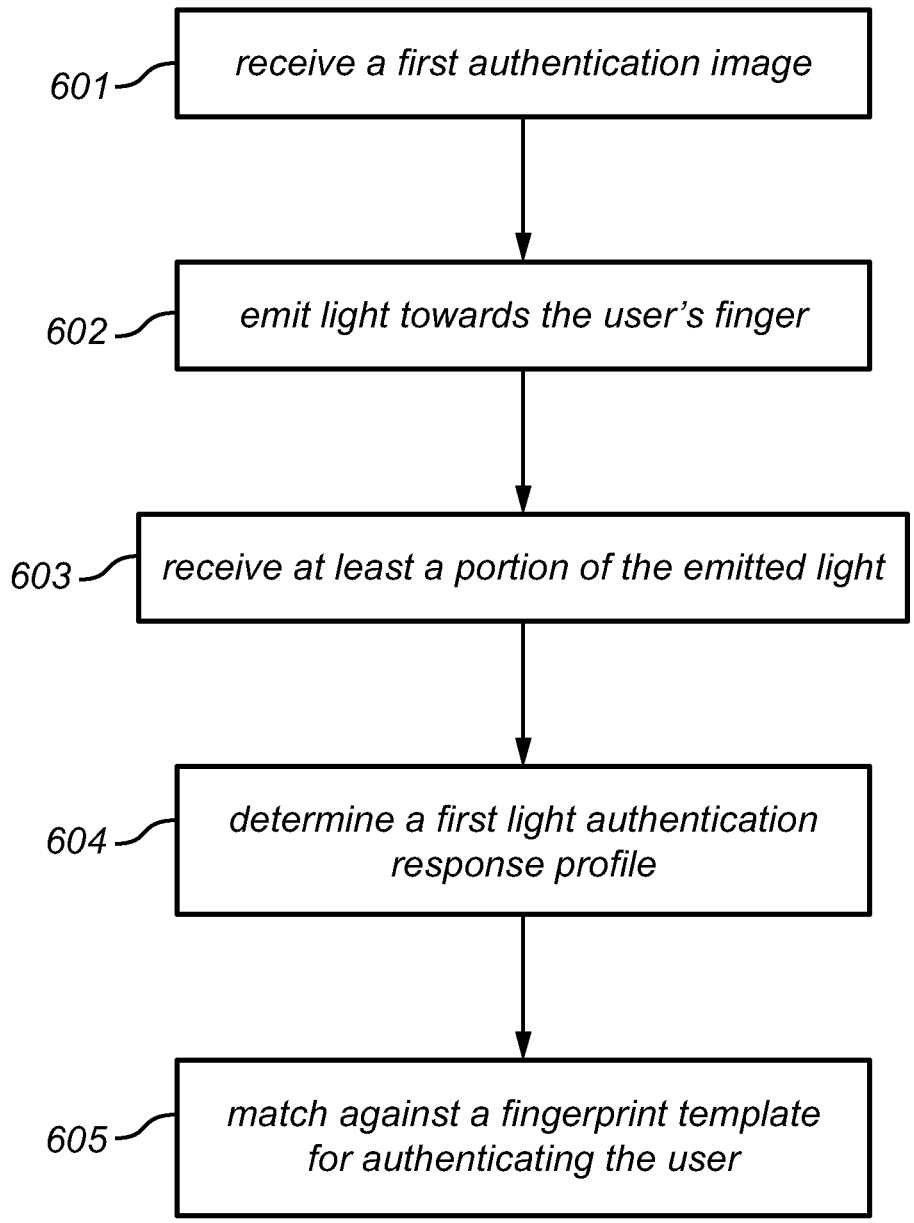
FIG. 6 is a flow chart of a method for authenticating a user of an electronic device according to an example embodiment.

Now, in order to describe a method of enrolling a fingerprint, as well as a method for authenticating a user of an electronic device 100, by using one of the above described fingerprint detection arrangements 102, 402 described above in relation to FIGS. 2-4, reference is made to FIGS. 5 and 6 in combination with particularly FIGS. 3a-3b.

Reference is first made to FIG. 5 which illustrates a flow chart of a method of enrolling a fingerprint of a user's finger according to an example embodiment.

Firstly, when enrolling the fingerprint, the user of the electronic device 100 places his finger 202 on the exterior surface 110 of the fingerprint detection arrangement 102, 402. This position is set as the first position. The fingerprint sensor 101 hereby captures 501 a first enrollment image of the fingerprint of the user's finger 202. The first enrollment image is thus specific for the captured image when the finger 202 is placed at the specific first position on the fingerprint sensor 101. The light emitting device 132 thereafter, or simultaneously, emits 502 light towards the user's finger 202, which emitted light is received 503 by the light receiving device 134. Based on the received light by the light receiving device 134, a first light response profile is determined 504. As described above, the light response profile is preferably based on the intensity $I_1$ of the light received at the light receiving device 134. More preferably, the light response profile is based on the difference between the light intensity $I_1$ of the light received at the light receiving device 134 and the light intensity $I_{em}$ emitted from the light emitting source 132. Thereafter, a fingerprint template can be formed 505, which fingerprint template comprises a representation based on the first enrollment image and the first light response profile. In more detail, for a specific first position of the finger 202 on the fingerprint sensor 101, there is provided an image of the fingerprint captured by the fingerprint sensor 101 as well as a light response profile based on the light intensity for such first position of the finger 202 on the fingerprint sensor 101.

The enrollment of the user's finger thereafter preferably continues by positioning the finger 202 at a plurality of positions on the fingerprint sensor 101, whereby each position will be associated with a specific captured image and a specific light response profile.

When using a fingerprint detection arrangement 402 as depicted in FIG. 4, the step of emitting light may be performed by a selected one of the plurality of light emitting devices 132, and the step of receiving the emitted light may be performed by a selected one of the plurality of light receiving devices 134. The specific light emitting device 132 and light receiving device 134 used may be based on the specific position of the finger, which position is determined by the fingerprint sensor 101. Alternatively, each of the plurality of light emitting sources 132 emits light and each of the light receiving devices 134 receives light, whereby a light response is formed by combining light intensity data of the light received by the light receiving devices 134.

Reference is now made to FIG. 6 which illustrates a flow chart of a method for authenticating a user of the electronic device 100 according to an example embodiment.

First, when trying to gain access to the electronic device 100, the user places his finger 202 on the exterior surface 110 of the fingerprint detection arrangement 102, 402. Hereby, a first authentication image of the fingerprint of the user's finger is received 601. The light emitting device 132 thereafter, or simultaneously, emits 602 light towards the user's finger 202, which emitted light is received 603 by the light receiving device 134. Based on the received light by the light receiving device 134, a first light authentication response profile is determined 604. The first authentication image and the first light authentication response profile are matched 605 against a fingerprint template formed according to the above description in relation to FIG. 5. Hence, the first authentication image and the first light authentication response profile is matched against a fingerprint template comprising a fingerprint representation for a finger of the user for at least one previously enrolled position of the finger at the fingerprint sensor and an associated light response profile.

In the present context, an enrolled fingerprint should be understood to correspond to the fingerprint data of the user's finger which the user "previously" provided when activated/registered himself, as described above, with the fingerprint detection arrangement. Hence, the enrolled fingerprint corresponds to the fingerprint, or fingerprints, of the user of the electronic device. Within the context of the present disclosure, the expression "fingerprint data" should be interpreted broadly and to include both a regular "visual image" of a fingerprint of a finger as well as a set of measurements relating to the finger when acquired using the fingerprint sensor. Similarly, the "light response profile" corresponds to previously acquired metadata in the form of optical light for the specific position of the user's finger at the fingerprint sensor.

Moreover, the expression "processing circuitry" should be understood to include any type of computing device, such as an ASIC, a micro-processor, etc. It should also be understood that the actual implementation of such a processing circuitry may be divided between more than a single device/circuit.

The control functionality of the present disclosure may be implemented using existing control units or computer processors, or by a special purpose computer processor for an appropriate system, incorporated for this or another purpose, or by a hardwire system. Embodiments within the scope of the present disclosure include program products comprising machine-readable medium for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a sequence the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Additionally, even though the invention has been described with reference to specific exemplifying embodiments thereof, many different alterations, modifications and the like will become apparent for those skilled in the art.

Even though the invention has been described with reference to specific exemplifying embodiments thereof, many different alterations, modifications and the like will become apparent for those skilled in the art. Also, it should be noted that parts of the device may be omitted, interchanged or arranged in various ways, the sensor device yet being able to perform the functionality of the present invention. For example, the fingerprint sensor may be positioned on a side portion or on the backside of the electronic device. Hence, the present invention should not be construed as limited to a specific position of the fingerprint sensor.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A method of enrolling a fingerprint of a user's finger, by means of a fingerprint detection arrangement comprising a fingerprint sensor and an optical sensor and a light receiving device, the method comprising:
   capturing, by the fingerprint sensor, a first enrollment image of a fingerprint of a user's finger placed on the fingerprint sensor at a first position thereon;
   emitting light, by the light emitting source of the optical sensor, towards the user's finger;
   receiving, by the light receiving device at least a portion of the light emitted by the light emitting source when the finger is placed at the first position on the fingerprint sensor;
   determining a first light response profile based on the light received by the light receiving device; and
   forming a fingerprint template comprising a fingerprint representation based on the first enrollment image and the first light response profile by combining the first enrollment image and the first light response profile when the finger is placed at the first position of the fingerprint sensor.

2. The method according to claim 1, wherein determining the first light response profile is further based on the light emitted by the light emitting source.

3. The method according to claim 1, wherein determining the first light response profile comprises:
- determining an emitted light intensity of the light emitted by the light emitting source;
- determining a received light intensity of the light received by the light receiving device;
- comparing the received light intensity with the emitted light intensity; and
- determining the first light response profile based on a difference in light intensity between the received light intensity and the emitted light intensity.

4. The method according to claim 1, wherein the light emitting device is arranged to emit light of at least two distinct wavelengths, and the light receiving device is arranged to receive at least a portion of the light of the at least two distinct wavelengths.

5. The method according to claim 1, further comprising:
- determining the first position on the fingerprint sensor based on the enrollment image captured by the fingerprint sensor.

6. The method according to claim 5, wherein the optical sensor is a first optical sensor comprising a first light emitting source and a first light receiving device, wherein the fingerprint detection arrangement further comprises a second optical sensor comprising a second light emitting source and a second light receiving device, wherein the method further comprises:
- comparing the determined first position on the fingerprint sensor with at least a first and a second pre-set finger position on the fingerprint sensor;
- controlling the first optical sensor to emit light by the first light emitting source and to receive at least a portion of the emitted light by the first light receiving device if the first position substantially corresponds to the first pre-set finger position.

7. The method according to claim 6, further comprising:
- inhibiting the second optical sensor from emitting light if the first position substantially corresponds to the first pre-set finger position.

8. The method according to claim 1, further comprising:
- capturing, by the fingerprint sensor, a second enrollment image of the fingerprint of the user's finger placed on the fingerprint sensor at a second position thereon, the second position being different in comparison to the first position;
- emitting light, by the light emitting source of the optical sensor, towards the user's finger;
- receiving, by the light receiving device, at least a portion of the light emitted by the light emitting source when the finger is placed at the second position on the fingerprint sensor; and
- determining a second light response profile based on the light received by the light receiving device when the finger is placed at the second position on the fingerprint sensor;
- wherein forming the fingerprint template comprising the fingerprint representation is further based on the second enrollment image and the second light response profile when the finger is placed at the second position.

9. The method according to claim 8, wherein the second position of the user's finger corresponds to a position being rotated on a surface of the fingerprint sensor relative to the first position.

10. The method according to claim 8, wherein the second position of the user's finger corresponds to a position being moved along a surface of the fingerprint sensor relative to the first position.

11. The method according to claim 1, wherein the fingerprint sensor is one of a capacitive fingerprint sensor and an ultrasound fingerprint sensor.

12. A method for authenticating a user of an electronic device comprising a fingerprint detection arrangement, the fingerprint detection arrangement comprising a fingerprint sensor and an optical sensor comprising a light emitting source and a light receiving device, the method comprising:
- receiving, by the fingerprint sensor, a first authentication image of a fingerprint of a user's finger placed on the fingerprint sensor;
- emitting light, by the light emitting source of the optical sensor, towards the user's finger;
- receiving, by the light receiving device at least a portion of the light emitted by the light emitting source when the finger is placed on the fingerprint sensor;
- determining a first light authentication response profile based on the light received by the light receiving device; and
- matching the first authentication image and the first light authentication response profile against a fingerprint template for authenticating the user, wherein the fingerprint template comprises a fingerprint representation for a finger of the user for at least one previously enrolled position of the finger at the fingerprint sensor and an associated light response profile.

13. The method according to claim 12, wherein matching the first authentication image and the first light authentication response profile against the fingerprint template further comprises:
- determining a position of the finger on the fingerprint sensor based on the first authentication image of the fingerprint.

14. The method according to claim 13, wherein matching the first authentication image and the first light authentication response profile against the fingerprint template further comprises:
- determining a correspondence between the determined position of the finger on the fingerprint sensor and the fingerprint representation for the finger of the user for the at least one previously enrolled position.

15. A fingerprint detection arrangement comprising a fingerprint sensor and an optical sensor, the optical sensor comprising a light emitting source and a light receiving device, and a control unit connected to the fingerprint sensor and the optical sensor, wherein, when a user enrolls a fingerprint, the control unit is configured to:
- control the fingerprint sensor to capture a first enrollment image of a fingerprint of a user's finger when the finger is placed on the fingerprint sensor at a first position thereon;
- control the light emitting source of the optical sensor to emit light towards the user's finger;
- control the light receiving device to receive at least a portion of the light emitted by the light emitting source when the finger is placed at the first position on the fingerprint sensor;
- determine a first light response profile based on the light received by the light receiving device; and
- form a fingerprint template comprising a fingerprint representation based on the first enrollment image and the first light response profile by combining the first enrollment image and the first light response profile when the finger is placed at the first position of the fingerprint sensor.

16. A fingerprint detection arrangement of an electronic device, the fingerprint detection arrangement comprising a fingerprint sensor and an optical sensor, the optical sensor comprising a light emitting source and a light receiving device, and a control unit connected to the fingerprint sensor and the optical sensor, wherein, when authenticating a user of the electronic device, the control unit is configured to:
control the fingerprint sensor to receive a first authentication image of a fingerprint of a user's finger when the finger is placed on the fingerprint sensor;
control the light emitting source of the optical sensor to emit light towards the user's finger;
control the light receiving device to receive at least a portion of the light emitted by the light emitting source when the finger is placed at the first position on the fingerprint sensor;
determine a first light authentication response profile based on the light received by the light receiving device; and
match the first authentication image and the first light authentication response profile against a fingerprint template for authenticating the user, wherein the fingerprint template comprises a fingerprint representation for a finger of the user for at least one previously enrolled position of the finger at the fingerprint sensor and an associated light response profile.

* * * * *